US009915642B2

(12) United States Patent
Ribble

(10) Patent No.: US 9,915,642 B2
(45) Date of Patent: Mar. 13, 2018

(54) METHOD FOR ASSESSING THE CONDITION OF A TISSUE SAMPLE WITH COHERENT ELECTROMAGNETIC RADIATION

(71) Applicant: Hill-Rom Services, Inc., Batesville, IN (US)

(72) Inventor: David Ribble, Indianapolis, IN (US)

(73) Assignee: Hill-Rom Services, Inc, Batesville, IN (US)

( * ) Notice: Subject to any disclaimer, the term of this patent is extended or adjusted under 35 U.S.C. 154(b) by 0 days.

(21) Appl. No.: 15/090,981

(22) Filed: Apr. 5, 2016

(65) Prior Publication Data

US 2016/0299121 A1    Oct. 13, 2016

Related U.S. Application Data

(60) Provisional application No. 62/146,607, filed on Apr. 13, 2015, provisional application No. 62/153,134, filed on Apr. 27, 2015.

(51) Int. Cl.
*G01B 9/02* (2006.01)
*G01N 33/483* (2006.01)
*G01N 21/47* (2006.01)
*A61B 5/00* (2006.01)

(52) U.S. Cl.
CPC ....... *G01N 33/4833* (2013.01); *A61B 5/0066* (2013.01); *A61B 5/445* (2013.01); *G01B 9/02088* (2013.01); *G01B 9/02091* (2013.01); *G01N 21/47* (2013.01);
(Continued)

(58) Field of Classification Search
CPC . G01N 21/47; G01N 21/4795; G01B 9/02091
See application file for complete search history.

(56) References Cited

U.S. PATENT DOCUMENTS

2009/0018436 A1* 1/2009 Gey Van Pittius .. A61B 5/0059
                                                                   600/425
2015/0327777 A1   11/2015 Kostic et al.
2016/0040976 A1*  2/2016 Berkeley .............. G01N 21/359
                                                                   356/479

FOREIGN PATENT DOCUMENTS

DE          10034251 C1      6/2001

OTHER PUBLICATIONS

European Search Report for EP Application 16164398.6, dated Sep. 14, 2016; Place of Search—Munich; Date of Completion of the search—Sep. 2, 2016.
(Continued)

*Primary Examiner* — Jonathan Hansen

(57) ABSTRACT

A method of assessing a tissue sample includes the steps of:
1) splitting source electromagnetic radiation into:
   a) sample arm radiation directed in a Z direction toward a sample thereby illuminating the sample at a first selected XY coordinate pair of the sample, and
   b) reflector arm radiation directed toward a reflector so that the reflector arm radiation travels a path length;
2) interfering sample-scattered electromagnetic radiation with reflector-reflected electromagnetic radiation thereby establishing an interference pattern associated with the sample;
3) comparing the sample interference pattern to a reference interference pattern; and
4) reaching a conclusion about the sample based on the comparison.

12 Claims, 13 Drawing Sheets

(52) U.S. Cl.
CPC ... *G01N 21/4795* (2013.01); *G01N 2201/068* (2013.01); *G01N 2201/06113* (2013.01)

(56) References Cited

OTHER PUBLICATIONS

Optical Non-Invasive Approaches to Diagnosis of Skin Diseases, Nikiforos Kollias and Georgios N. Stamatas; Johnson and Johnson Consumer Products Co., Skillman, New Jersey, USA, XP-002321055; vol. 7, No. 1 Dec. 2002.

A Survey of Optical Imaging Techniques for Assessing Wound Healing; Albert H. Zhou; International Journal of Intelligent Control and Systems; vol. 71, No. 3, Sep. 2012, 79-85.

Rafat R. Ansari et al. A Non-Invasive Miniaturized-Wireless Laser-Doppler Fiber-Optic Sensor for Understanding Distal Fingertip Injuries in Astronauts; MIT Open Access Articles; Publisher—The International Society for Optical Engineering; Proc. of SPIE vol. 7186 718609-8.

James G. Fujioto; Optical coherence tomography; Department of Electrical Engineering and Computer Science and Research Laboratory of Electronics, Massachusetts Institute of Technology, Cambridge, MA 02139, USA; C. R. Acad. Sci. Paris 1.2, Serie IV, p. 1099-1111, 2001.

David Huang et al.; Optical Coherence Tomography; Science, New Series, vol. 254, o. 5035 (Nov. 22, 1991), 1178-1181; American Association for the Advancement of Science.

\* cited by examiner

METHOD FOR ASSESSING THE CONDITION OF A TISSUE SAMPLE WITH COHERENT ELECTROMAGNETIC RADIATION

CROSS REFERENCE TO RELATED APPLICATIONS

This application claims priority to U.S. provisional application 62/146,607 entitled "Method for Assessing the Condition of a Tissue Sample with Electromagnetic Radiation" filed on Apr. 13, 2015 and U.S. provisional application 62/153,134 entitled "Method for Assessing the Condition of a Tissue Sample with Coherent Electromagnetic Radiation" filed on Apr. 27, 2015. The contents of both applications are incorporated herein by reference.

TECHNICAL FIELD

The subject matter described herein relates to the use of coherent electromagnetic radiation for assessing the condition of a tissue sample. One example application is detection of a pressure ulcer or a tissue condition which is a precursor to a pressure ulcer.

BACKGROUND

Nurses, physicians and others involved in the care of patients may need to assess the condition of a patient's tissue for abnormalities. One abnormality of interest is a pressure ulcer. One definition of a pressure ulcer is the International NPUAP-EPUAP Pressure Ulcer Definition which advises "A pressure ulcer is localized injury to the skin and/or underlying tissue usually over a bony prominence, as a result of pressure, or pressure in combination with shear." Pressure ulcers can develop and worsen quickly and can be life threatening. Another abnormality of interest is a deep tissue injury. The National Pressure Ulcer Advisory Panel (NPAUP) defines a deep tissue injury as "A pressure-related injury to subcutaneous tissues under intact skin. Initially, these lesions have the appearance of a deep bruise. These lesions may herald the subsequent development of a Stage III-IV pressure ulcer even with optimal treatment." (NPAUP, 2005). It is therefore desirable to be able to identify deep tissue injuries, pressure ulcers, and tissue conditions which are precursors to pressure ulcers or to at least be able to identify the early stages of these conditions (including at times when the condition may not be readily discernible) so that corrective intervention can be taken before the condition becomes life threatening or difficult to heal.

SUMMARY

A method for assessing the condition of a tissue sample includes the steps of:
1) splitting source electromagnetic radiation into:
   a) sample arm radiation directed in a Z direction toward a sample thereby illuminating the sample at a selected X-Y coordinate of the sample, and
   b) reflector arm radiation directed toward a reflector so that the reflector arm radiation travels a path length;
2) interfering sample-scattered electromagnetic radiation with reflector-reflected electromagnetic radiation thereby establishing an interference pattern associated with the sample;
3) comparing the sample interference pattern to a selected interference pattern; and
4) reaching a conclusion about the sample based on the comparison.

BRIEF DESCRIPTION OF THE DRAWINGS

The foregoing and other features of the various embodiments of the methods and apparatuses described herein will become more apparent from the following detailed description and the accompanying drawings in which.

DETAILED DESCRIPTION

Figure 1:
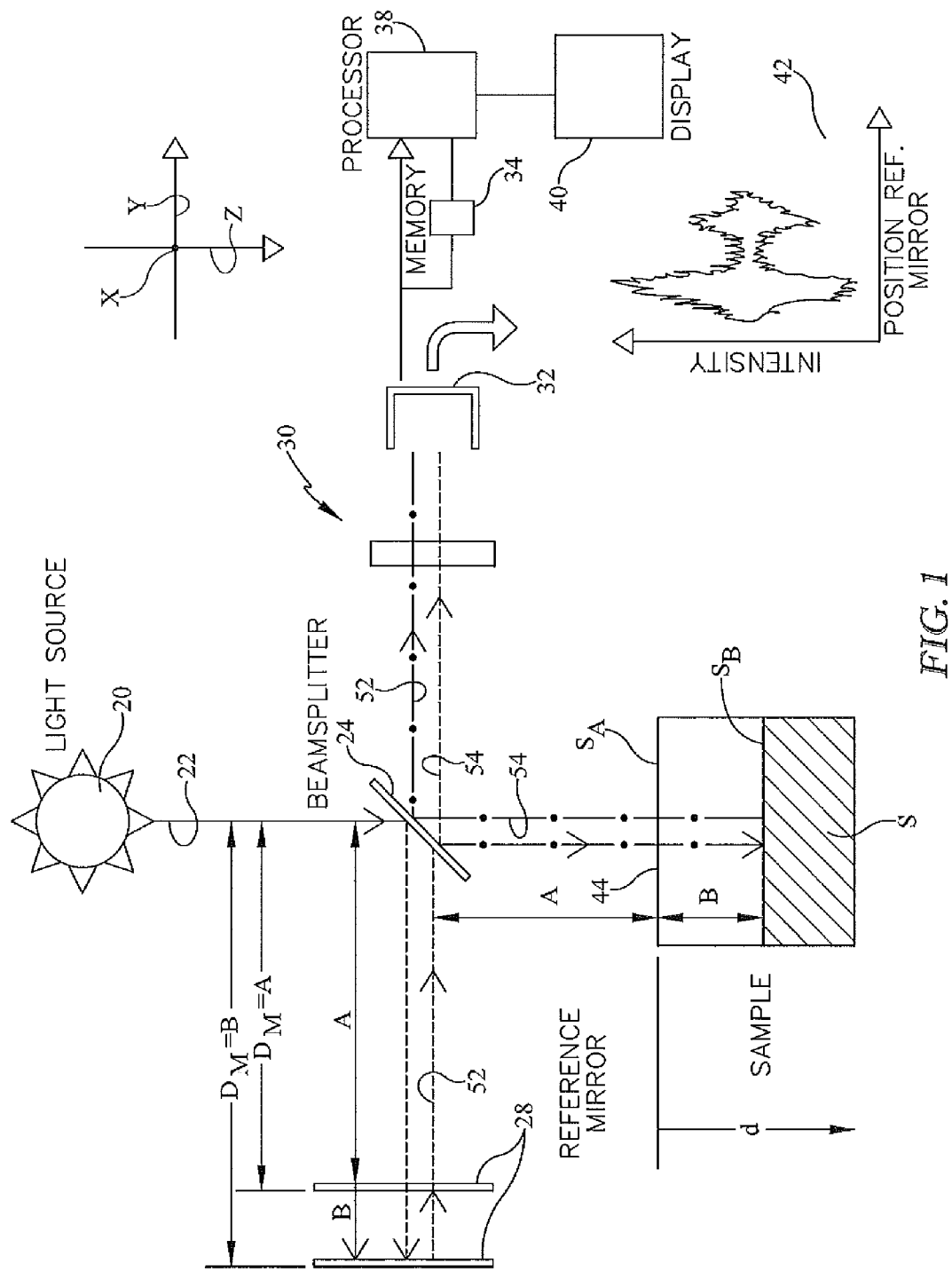
FIG. 1 is a schematic showing selected components of an apparatus for carrying out the method of assessing the condition of a tissue sample S as described herein, and which method involves comparing an interference pattern derived from a tissue sample to a reference interference pattern.

This specification describes methods which employ coherent electromagnetic radiation to assess the condition of a tissue sample, for example to determine if the sample exhibits an abnormal or unusual condition. One example tissue is skin. Example conditions include pressure ulcers, burns, and scars. In principle, the electromagnetic radiation can correspond to any part of the electromagnetic spectrum, however design considerations may commend the use of particular portions of the spectrum. For that reason, and to make the disclosure more concrete, this description will refer to electromagnetic radiation as light, without any intent to limit the generality of the disclosure or claims except when portions of the spectrum (e.g infrared, visible, ultraviolet) are expressly designated. In addition, the word "illuminate" and its variants and synonyms are not restricted to the visible portion of the spectrum but instead describe the act of causing the light (electromagnetic radiation) to be incident upon the tissue sample. In addition, "coherent light", as used herein, includes low coherence light, which is a subset of coherent light. In addition, although the examples used in this description are predominantly examples of pressure ulcers, the described apparatuses and methods may be equally applicable to other conditions such as deep tissue injuries and precursors to pressure ulcers.

In this specification features similar to or the same as features previously described may be identified by reference numerals which were previously used.

FIG. 1 is a schematic showing selected components of an apparatus 30 for carrying out the method of assessing the condition of a tissue sample S as described herein. The apparatus includes a source 20 of coherent light 22, a beamsplitter 24, a mirror 28, and a detector 32, for example a photodetector. The distance DM from the mirror to the beamsplitter is adjustable as indicated by the two positions A, B of the mirror. The apparatus also includes a memory 34 for storing information detected by the detector, a processor 38 for processing information from the detector, and a display 40 for displaying information. The illustration also includes Cartesian reference axes X, Y, and Z, and a graph 42 of light intensity as a function of mirror position.

Tissue sample S has an exposed surface 44. As explained below the condition of the sample can be evaluated at sampling sites on the surface such as SA and at subsurface sampling sites such as $S_B$. When sampling occurs at multiple sampling sites, all of which are approximately the same depth d beneath the surface (or at the surface where d=0), the plane of those sites can be referred to as a sampling plane.

During operation coherent light 22 from the source arrives at the beamsplitter. The beamsplitter splits the light causing the light to proceed along two paths. One path is a reflector path indicated with a dashed line. The reflector path includes a reflector arm which is a portion of the reflector path that extends between the beamsplitter and the mirror. Light which follows the reflector path reflects off the beamsplitter toward the mirror, reflects off the mirror, (after which the light can be referred to as reflector-reflected light 52), returns along the reflector arm to the beamsplitter, and passes through the beamsplitter toward detector 32. The other path is a sample path indicated with a dash-dot line (alternatively both the sample path and the reflector path could include the subpath extending from the light source to the beamsplitter). The sample path includes a sample arm which which is a portion of the sample path that extends between the beamsplitter and the sampling site, e.g. $S_A$ or $S_B$. Light which follows the sample path scatters off the sample (after which the light can be referred to as sample-scattered light 54). The sample-scattered light returns along the sample arm to the beamsplitter where it reflects off the beamsplitter, rejoins the reflector-reflected light, and travels toward the detector 32. Interference (i.e. an interference pattern) resulting from the recombination of the sample-scattered light and the reflector-reflected light is detected by the detector. If coherent light is used, certain positions of the mirror will cause the length of the sample path from some determinable tissue depth d to match the length of the reflector path within the coherence length of the light.

Figure 2:
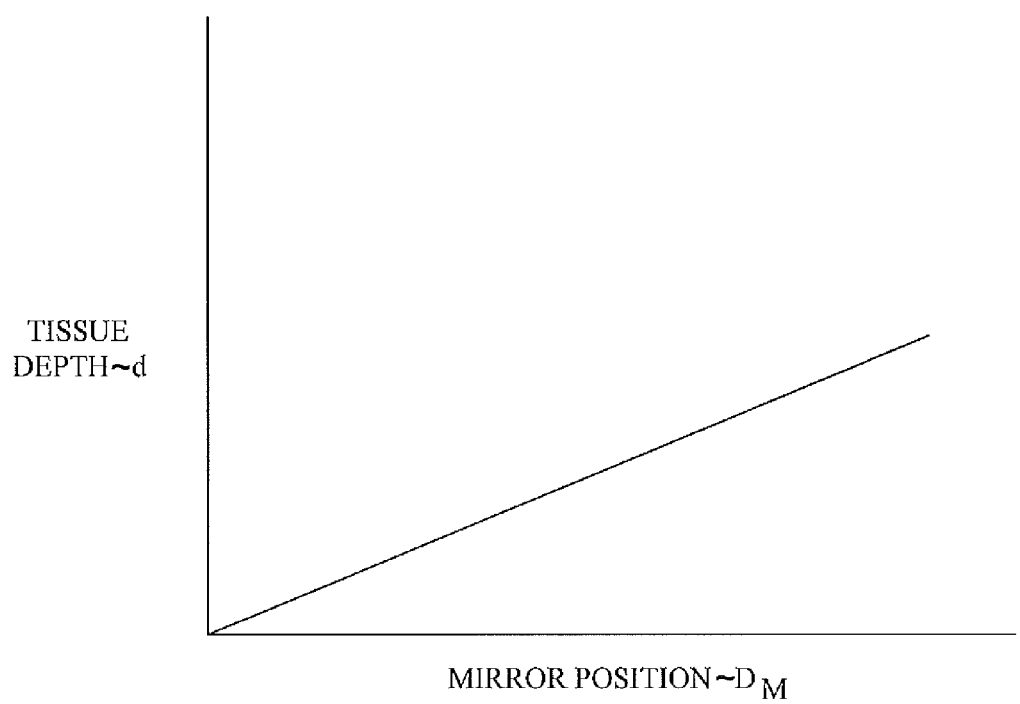
FIG. 2 is a graph showing a relationship between light intensity detected by the detector shown in FIG. 1 and position of the mirror shown in FIG. 1.

Therefore, as seen in FIG. 2, the sample-scattered light is light known to have been scattered from that depth d. FIG. 1 includes a graph 42 of light intensity detected by the detector as a function of mirror position.

It should be noted that most of the light incident on the sample is not reflected but instead scatters off at large angles and often multiple times. In conventional imaging, the diffusely scattered light contributes background noise that obscures the desired signal. The method described herein rejects most photons that scatter multiple times and therefore rejects background noise while collecting the desired signal, which is photons that are scattered only once or twice (rather than multiply scattered) from surfaces of interest.

The condition of the tissue sample at the sample site affects both the intensity and phase angle (or transit time) of the sample-scattered light relative to the intensity and phase angle (or transit time) of the reflector-reflected light. Therefore the condition of the sample affects the interference pattern detected at the detector. This sample interference pattern can be compared to a reference interference pattern which has been designated as conforming to a known condition (or to a documented but unknown condition). By way of example the comparison may employ strict, objective rules and/or more subjective guidelines to carry out the comparison. Further by way of example the rules may involve comparison of parameters of the interference patterns (e.g. inter-fringe spacing).

Based on the comparison, a conclusion can be reached about the condition of the sample. For example if the sample interference pattern compares favorably to the reference interference pattern, and the reference interference pattern corresponds to a known condition, it can be concluded that the sample exhibits the known condition. The sample interference pattern and the reference interference pattern do not necessarily have to be identical in all respects in order for the comparison to qualify as a favorable. A comparison in which the differences between the sample interference pattern and a reference interference pattern are no greater than some prescribed tolerance can be accepted as a favorable comparison.

If the sample interference pattern compares unfavorably to the reference interference pattern, and the reference interference pattern corresponds to a known condition, it can be concluded that the sample does not exhibit the known condition (although it may exhibit some other condition).

If the sample interference pattern compares favorably to the reference interference pattern, and the reference interference pattern corresponds to an unknown condition, it can be concluded that the sample exhibits the unknown condition.

Figure 3:
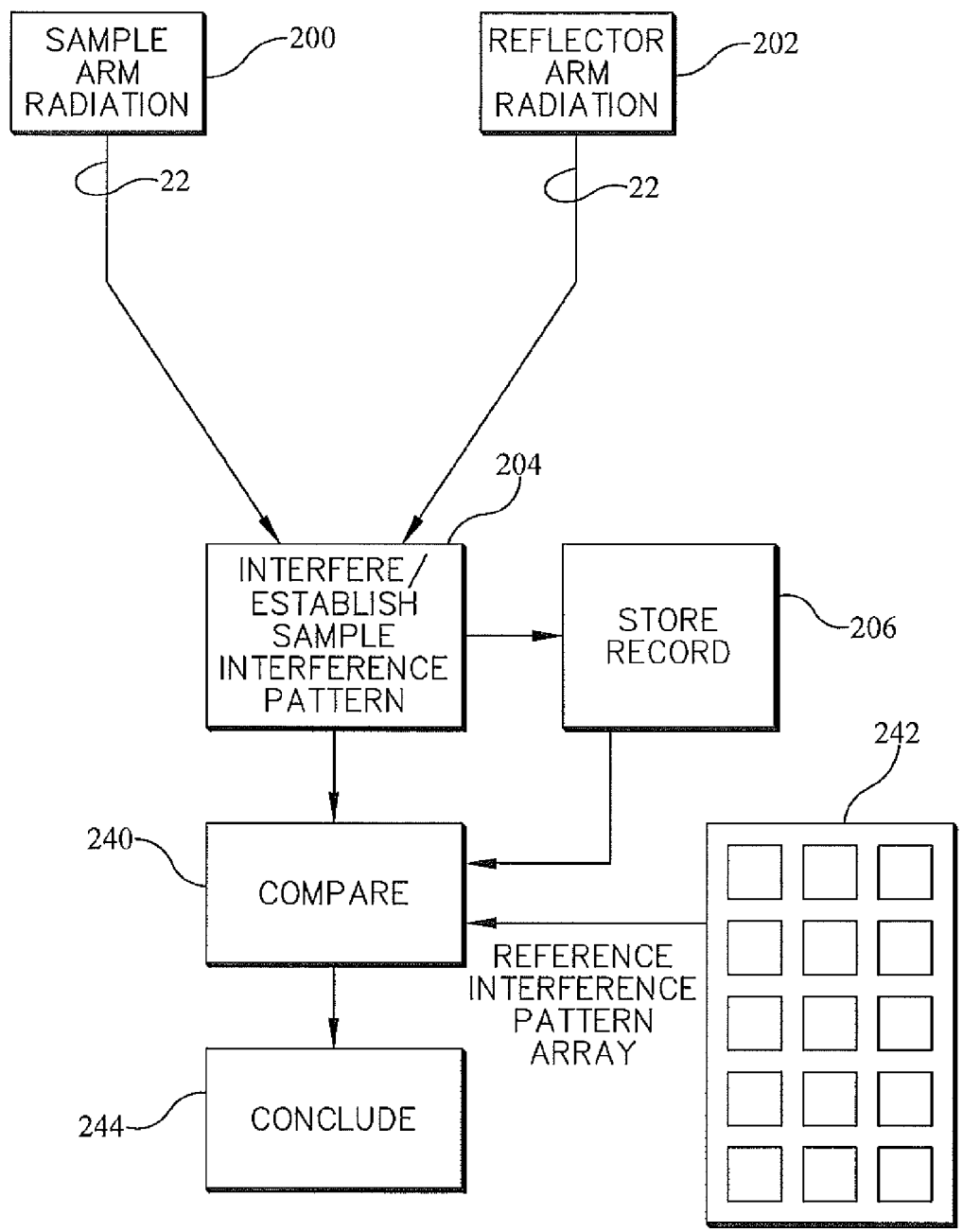
FIG. 3 is a block diagram showing a method of assessing the condition of a tissue sample using the apparatus of FIG. 1 and relying on a library of reference interference patterns.

FIG. 3 illustrates the foregoing in block diagram form. Blocks 200 and 202 represent coherent light 22 following the sample path and the reflector path respectively. At block 204 the sample scattered light and the reflector-reflected light are caused to interfere with each other and the sample interference pattern is established. A record of the sample interference pattern may be stored at block 206, for example in memory 34 of FIG. 1. Block 240 compares the sample interference pattern to a reference interference pattern. The reference interference pattern may be a member of a library 242 of interference patterns. Block 244 reaches a conclusion about the sample based on the comparison at block 240.

The comparing step of block 240 and the concluding step of block 244 can both be carried out by a processor such as processor 38 of FIG. 1. Alternatively steps 240, and 244 can both be carried out by a person. Alternatively step 240 can be carried out by a processor and the results of the comparison can be displayed on a display such as video monitor 40 or a hardcopy report. Step 244 can then be carried out by a person based on the displayed results of the comparison.

Figure 4:
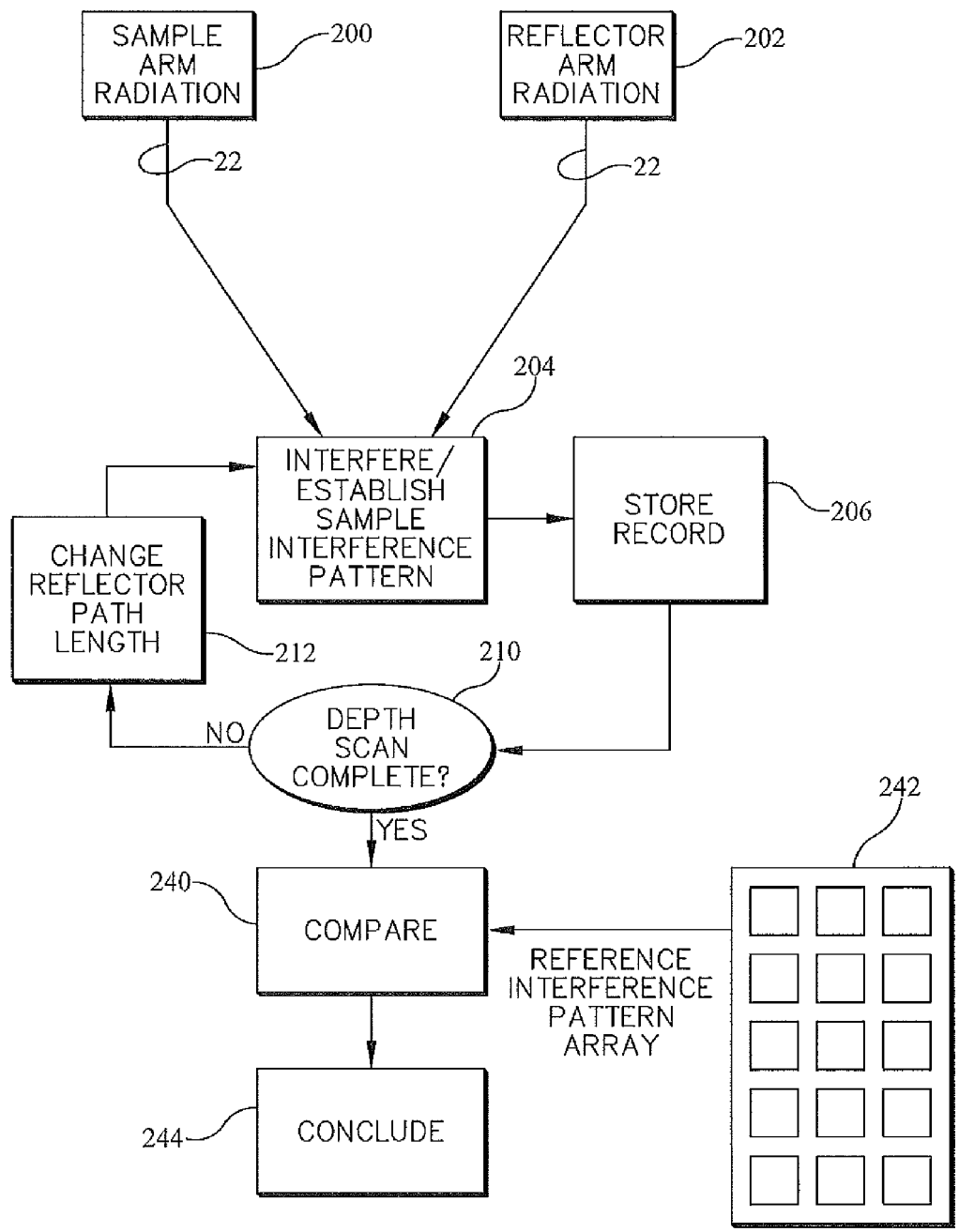
FIG. 4 is a block diagram similar to that of FIG. 3 showing a similar method in which the tissue is sampled at multiple depths.

The method as described so far is one in which the interference pattern is established at a single site, i.e. for a single reflector path length and for a single XY coordinate pair. This corresponds to a single point in the three dimensional XYZ coordinate system of FIG. 1. FIG. 4 shows a similar method in which the tissue is sampled at one or more additional depths d by adjusting the position of the mirror, for example from A to B in FIG. 1. This corresponds to sampling one or more additional sites (a total of two or more sites) along the Z axis but at the same X and Y coordinates. As seen in FIG. 4, block 210 tests whether the depth scan is complete, i.e. whether or not the tissue has been sampled at all the desired depths. If not the method proceeds to block 212 where the method specifies that the reflector path length should be changed to a different path length. The change in path length is effected by repositioning mirror 28. The method then proceeds again to step 204 where it establishes the sample interference pattern at the tissue depth corresponding to the adjusted position of the mirror. Thus, the establishment step 204 is carried out multiple times, once for each of different reflector path lengths, i.e. once for each of two or more tissue depths.

If the test at block 210 reveals that the depth scan has been completed, the method proceeds to blocks 240 and 244 to carry out the comparing and concluding steps. Because the method of FIG. 4 carries out the step of establishing a sample interference pattern at multiple depths (Z coordinates) the reference interference pattern is an array of interference patterns, one for each of the depths at which the sample interference pattern was established. The comparing step compares the sample interference patterns arising from the two or more establishing steps to the members of the reference interference pattern array. Two options for carrying out the comparing step are discussed below in connection with FIGS. 7-10.

Figure 5:
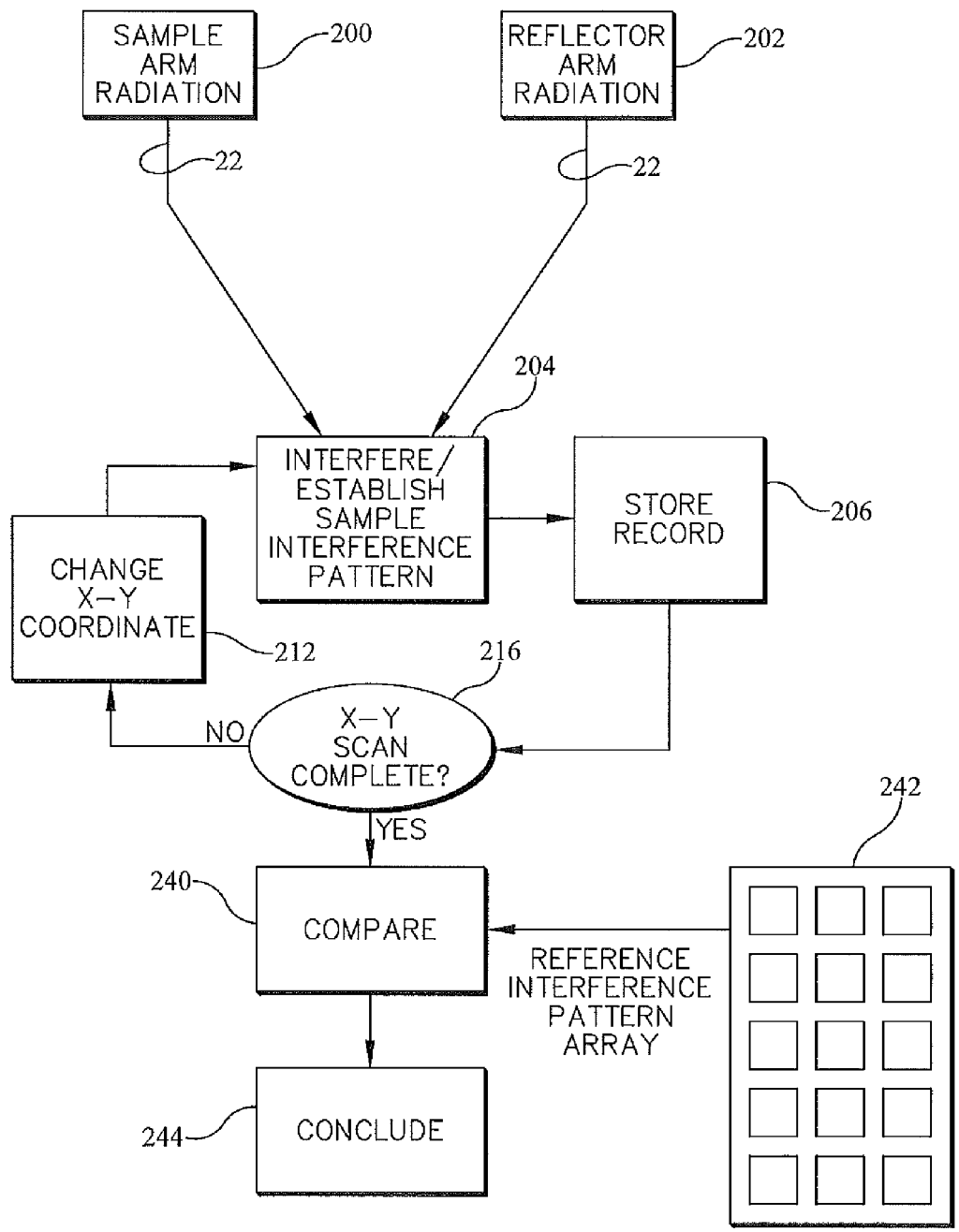
FIG. 5 is a block diagram similar to that of FIG. 3 showing an area-scan method in which sampling is carried out at multiple XY coordinates but at substantially a constant depth.

FIG. 5 shows an area-scan method. In contrast to the single coordinate method of FIG. 3, the area-scan method of FIG. 4 carries out the establishment test of block 204 at one or more additional XY coordinates but at substantially a constant depth (or, equivalently, substantially the same Z coordinate or substantially the same reflector path length). As used herein, an XY coordinate is considered to be an additional coordinate if the X coordinate or the Y coordinate or both the X and Y coordinates differ from all of the XY coordinates at which the establishment step had been previously carried out. This corresponds to sampling one or more additional sites (a total of two or more sites) at a different XY coordinate pair but at the same Z coordinates. As seen in FIG. 5, block 216 tests whether the XY scan is complete, i.e. whether or not the tissue has been sampled at all the desired XY coordinate pairs. If not the method proceeds to block 212 where the method changes the X coordinate, the Y coordinate, or both. The method then proceeds again to step 204 where it establishes the sample interference pattern at the selected XY coordinates. Thus, the establishment step 204 is carried out multiple times, once for each of two or more XY coordinates.

When the test at block 216 reveals that the XY scan has been completed, the method proceeds to blocks 240 and 244 to carry out the comparing and concluding steps. Because the method of FIG. 5 carries out the step of establishing a sample interference pattern at multiple XY coordinates, the reference interference pattern is an array of interference patterns, one for each of the XY coordinates at which the sample interference pattern was established. The comparing step compares the sample interference patterns arising from the two or more establishing steps to the members of the reference interference pattern array.

Figure 6:
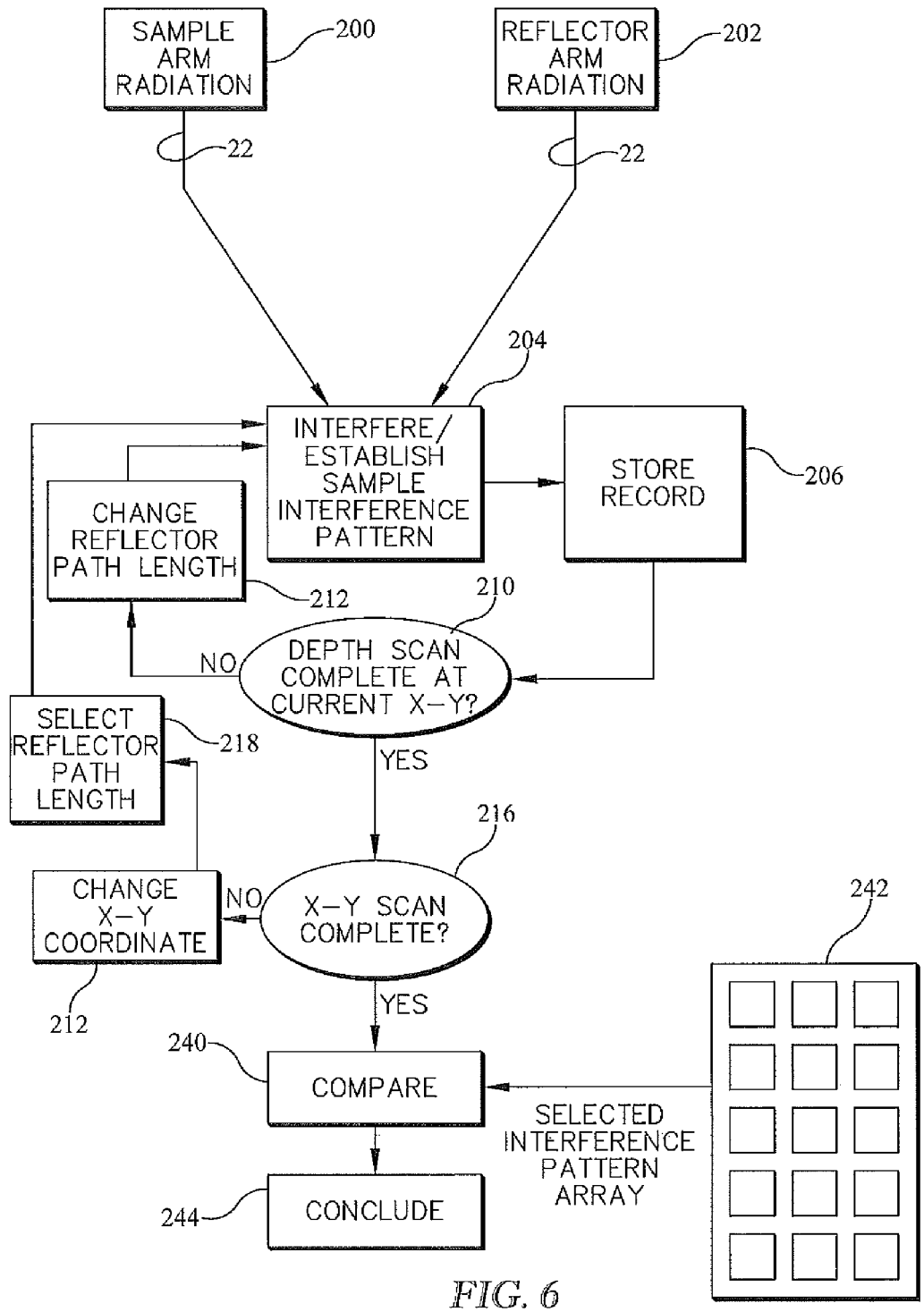
FIG. 6 is a block diagram showing a volume-scan method that combines the depth scan of FIG. 4 and the area scan of FIG. 5.

FIG. 6 is a block diagram showing a volume-scan method. The volume-scan method combines the depth scan of FIG. 4 and the area scan of FIG. 5. Block 210 tests whether the depth scan has been completed. If not the method proceeds to block 212 where the method specifies that the reflector path length should be changed to a different path length. The change in path length is effected by repositioning mirror 28. The method continues to repeat the step of establishing interference patterns at block 204 until the test at block 210 is satisfied. The method then proceeds to block 216 which tests whether the XY scan has been completed. If not, the method proceeds to block 212 where the XY coordinate is changed and then to block 218 where the reflector path length (Z coordinate) is selected by appropriate adjustment of the position of mirror 28. Selection of the Z coordinate may involve moving the mirror back to the first of the mirror positions used during the previous pass through the depth scan cycle (the loop defined by blocks 204, 206, 208, 212). Alternatively, selection of the Z coordinate may involve nothing more than keeping the mirror at its existing position (the last position used at the previous XY coordinates). At each subsequent pass through the depth scan cycle block 212 would then call for the mirror to return towards its starting position.

The method then proceeds to block 204 and executes the required number of depth scan cycles by looping through blocks 204, 206, 210 and 212. After completion of the depth scan cycles the method returns to block 216. When the test at block 216 is satisfied the method proceeds to blocks 240 and 244 to carry out the comparing and concluding steps. Because the method of FIG. 6 carries out the step of establishing a sample interference pattern at multiple Z coordinates and at multiple XY coordinates, the reference interference pattern is an array of interference patterns, one for each of the XYZ coordinates at which the sample interference pattern was established. The comparing step compares the sample interference patterns arising from the two or more establishing steps to the members of the reference interference pattern array.

The foregoing examples describe comparing a single sample interference pattern to a single reference interference pattern (or comparing a single sample interference pattern array to a single reference interference pattern array). In practice the sample interference pattern or array would be compared to multiple members of the library until the method either identified a favorable comparison or failed to do so after having compared the sample interference pattern against a satisfactory collection of the library members. A satisfactory collection could be a collection that includes all members of the library or could be a collection that includes only those members of the library that might be reasonably expected to yield a favorable comparison. In one example, if a caregiver suspects that that the tissue sample might exhibit characteristics consistent with a pressure ulcer, a satisfactory collection of library members could be a collection limited to those members known to represent pressure ulcers. In another example if a caregiver has no suspicion that the sample exhibits any particular condition, but merely wishes to monitor for the possible onset of some condition of concern, for example precursors to a pressure ulcer, a satisfactory collection of library members could be limited, once again, to a collection of those library members known to represent pressure ulcers.

If the sample interference pattern compares favorably to a reference interference pattern, and the reference interference pattern corresponds to a known condition, it could be concluded that the sample exhibits the known condition. One option is to discontinue the method as soon as a favorable comparison leads to the conclusion that the sample exhibits a known condition. Another option is to continue comparing the interference pattern of the sample to that of other members of the satisfactory collection until the interference pattern of the sample has been compared to those of all the members of the satisfactory collection. One or more satisfactory comparisons leads to the conclusion that the tissue sample exhibits at least one of the conditions represented by the collection.

If the sample interference pattern compares unfavorably to a reference interference pattern, and the reference interference pattern corresponds to a known condition, it can be concluded that the sample does not exhibit the known condition (although it may exhibit some other condition). If the interference pattern of the tissue sample of interest is compared to all the interference patterns of the satisfactory collection, it can be further concluded that none of the reference interference patterns in the satisfactory collection of reference interference patterns compares favorably to the interference pattern of the sample S of interest. Accordingly, none of the conditions represented by the reference interference patterns are present in the sample S of interest.

If the sample interference pattern compares favorably to the reference interference pattern, and the reference interference pattern corresponds to an unknown condition, it can be concluded that the sample exhibits the unknown condition. This might also be considered to be a conclusion that the condition of sample S is indeterminate. Other circumstances may also give rise to the conclusion that the condition of the sample is indeterminate. For example if the tissue sample interference pattern compares favorably to a large number of reference pattern interference patterns the conclusion could be that the condition of the sample is indeterminate. In another example the conclusion of indeterminacy could arise if the tissue sample interference pattern compares favorably to a small number (greater than one) of reference interference pattern, but the reference interference patterns are known to conform to conditions that are unlikely to occur together.

Figure 7:
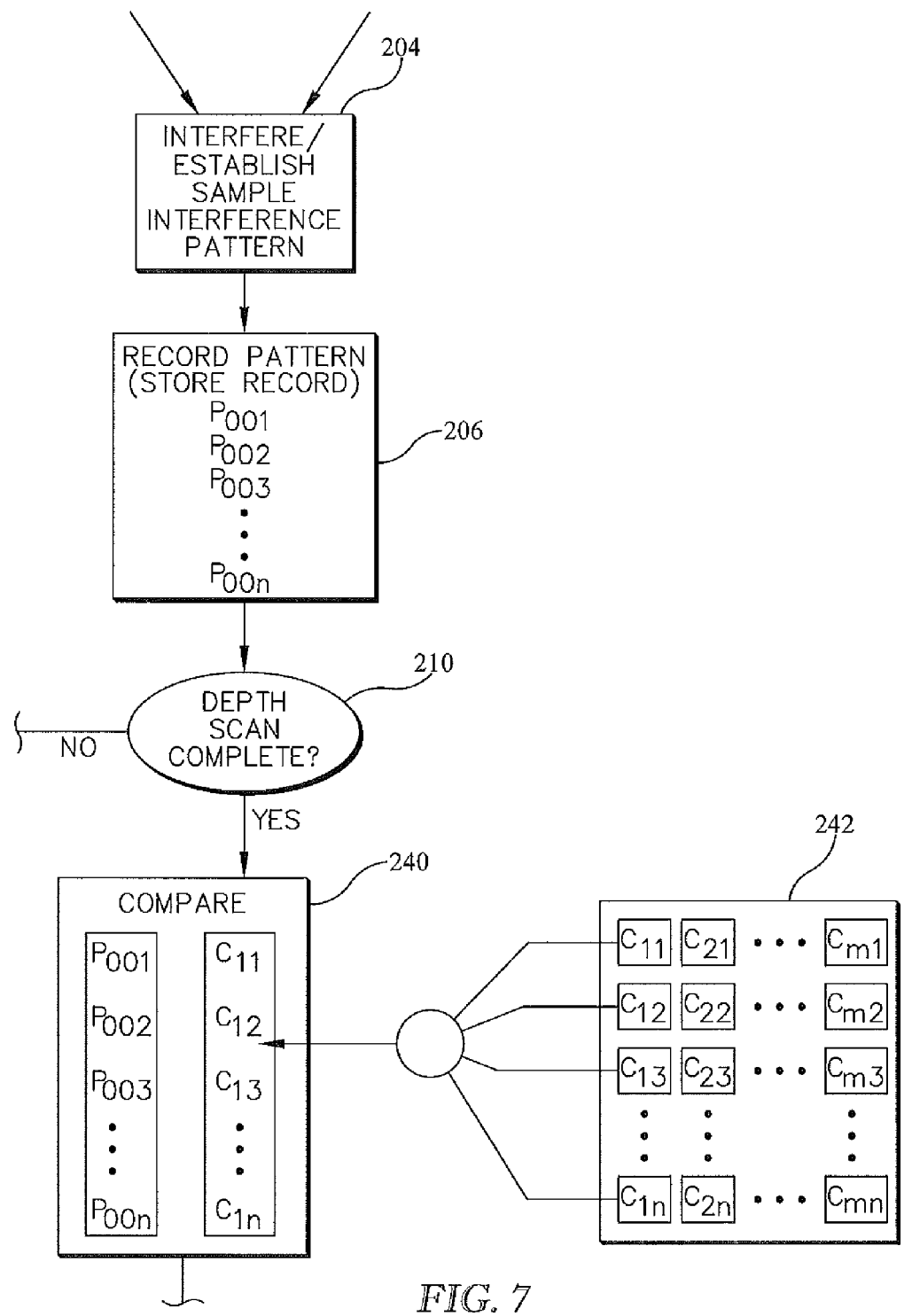
FIG. 7 is a partial block diagram showing an example of a specific option in which the comparing step of FIGS. 4-6 treats a set of sample interference patterns as an aggregate and treats a set of reference interference patterns as an aggregate.

FIG. 7 shows an example of a specific option for carrying out comparing step 240. The example of FIG. 7 is based on a depth scan (FIG. 4) but applies to any of the foregoing or similar methods which involve sampling the tissue at multiple sample sites (e.g. the depth scan of FIG. 4, the area scan of FIG. 5 or the volumetric scan of FIG. 6). Block 206 shows the result of having recorded the sample interference patterns $P_{001}$ through $P_{00n}$ arising from an n-level depth scan. Once the depth scan is complete (block 210), the method proceeds to comparison block 240. At block 240 the sample interference patterns are treated as an aggregate as indicated by the border surrounding all the $P_{ijk}$ values. The interference patterns selected for comparison to the sample pattern can be denoted $C_{pq}$ where subscript p indicates some tissue condition (e.g. condition number 1, condition number 2, and so forth) and subscript q indicates the interference pattern expected to arise at a tissue depth of approximately q in tissue which exhibits condition P. In other words $C_{pq}$ is the interference pattern expected to be produced by a tissue sample at depth q if the sample exhibits condition P. In the example the reference interference patterns selected for comparison to $P_{001}$ through $P_{00n}$ are $C_{11}$ through $C_{1n}$. The selected reference interference patterns comprise the interference pattern array that will be used for comparison against the array of sample interference patterns $P_{001}$ through $P_{00n}$. Once again the border surrounding the $C_{pq}$ entries at block 240 indicates that the reference pattern is treated as an aggregate. The comparison step 240 compares the aggregate sample pattern to the aggregate reference pattern, rather than individually comparing $P_{001}$ to $C_{11}$, $P_{002}$ to $C_{12}$, $P_{00n}$ to $C_{1n}$. As a result of the aggregate nature of the comparison, and depending on the exact rules employed to carry out the comparison, a comparison might qualify as a favorable comparison as long as the sample pattern as a whole compares favorably to reference pattern as a whole even if one or more specific comparisons (e.g. comparison of $P_{001}$ to $C_{11}$) is unfavorable, or if one or more of the depth scans is unavailable or unusable or if one or more of the $C_{pq}$ interference patterns is unavailable or unusable).

Figure 8:
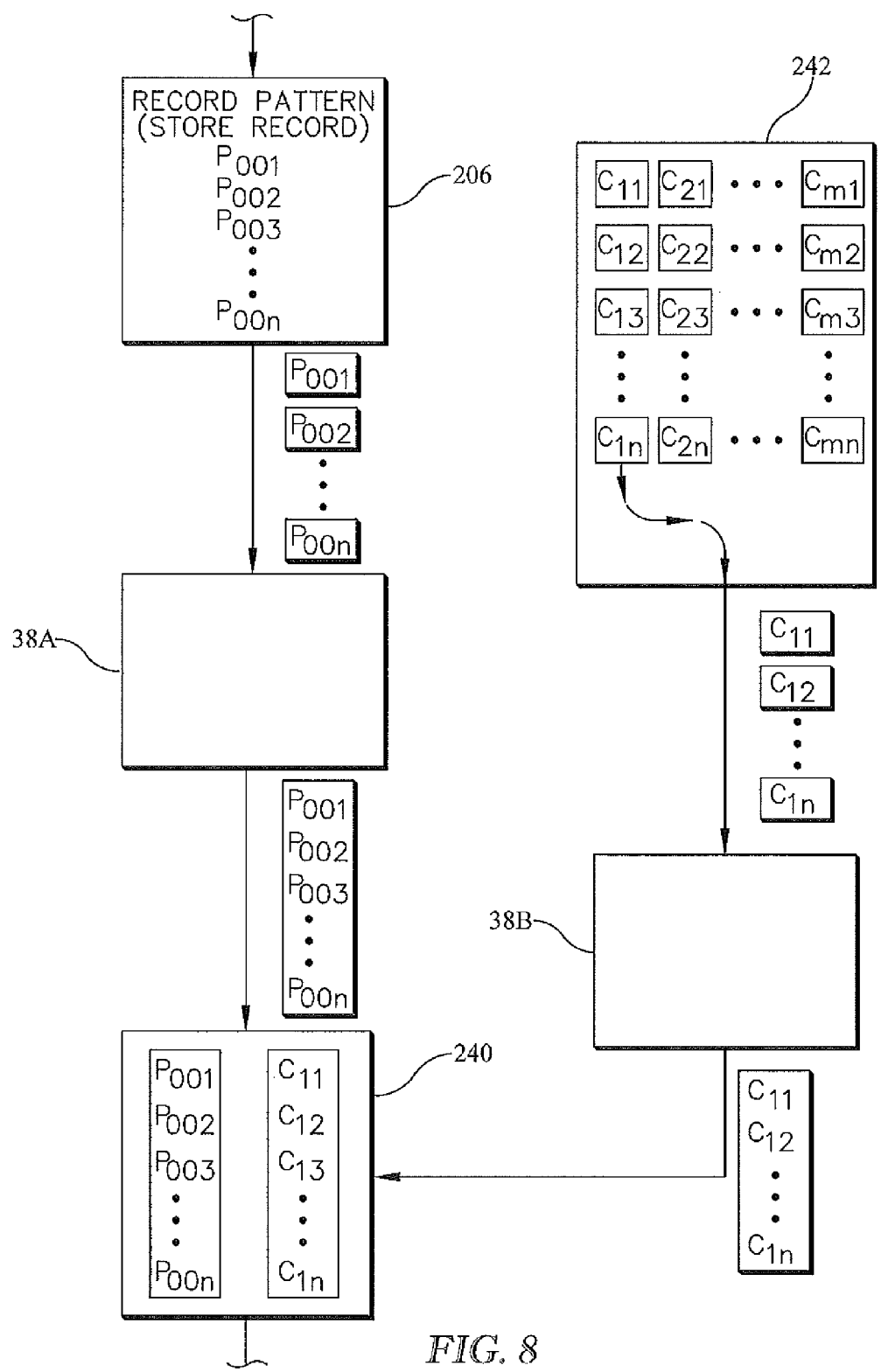
FIG. 8 is a partial block diagram showing one method for carrying out an aggregation option of FIG. 7.
Figure 9:
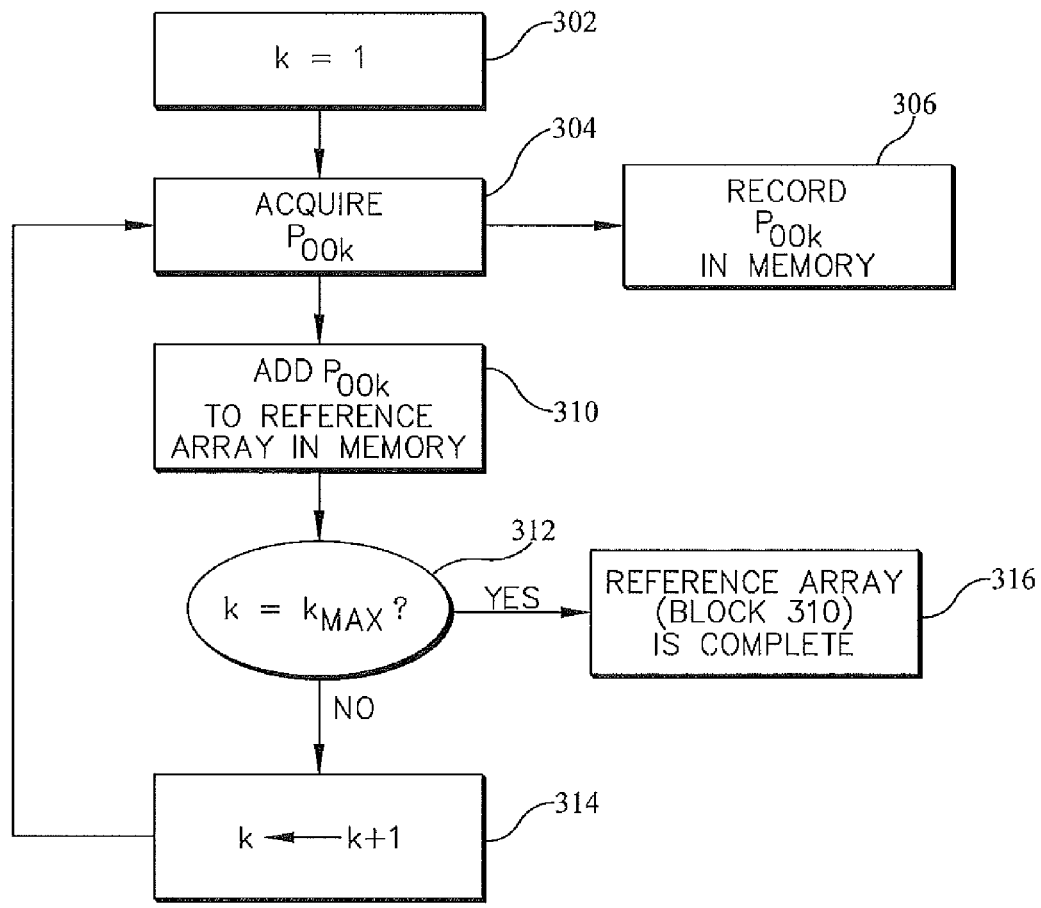
FIG. 9 is a partial block diagram showing an alternative method for carrying out the aggregation option of FIG. 7.

FIG. 7 suggests that the aggregation of the sample interference patterns and the aggregation of the reference interference patterns are carried out as part of the comparison step 240 based on the previously acquired interference patterns of individual elements ($P_{ijk}$ and $C_{pq}$) which may be stored in a memory device. However this need not be the case. FIG. 8 shows an example of a depth scan (FIG. 4) in which the aggregation is carried out by one or more processors such as 38A, 38B. The input to each processor is a set of individual elements. The output of each processor is an aggregation of the individual inputs. In another example, FIG. 9 shows a depth scan employing another alternative in which the individual interference patterns are progressively aggregated together at block 306 as they are acquired at block 304 instead of or in addition to being stored individually. Note that in the diagram of FIG. 9 the arrow symbol in block 314 signifies replacement of the current value of subscript k with the next higher value.

Figure 10:
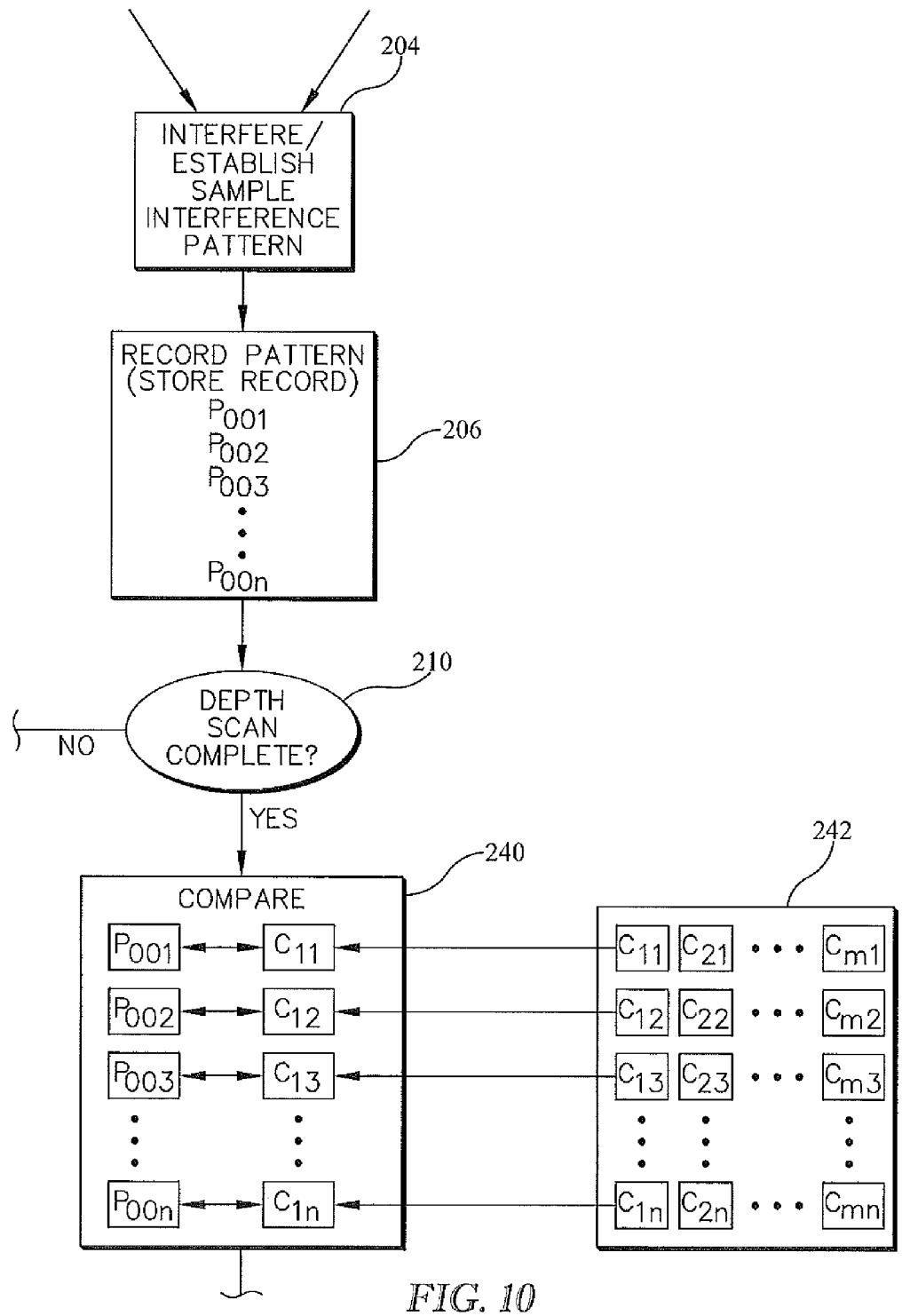
FIG. 10 is a partial block diagram similar to that of FIG. 7 showing an example of a specific option in which the comparing step of FIGS. 4-6 treats a set of sample interference patterns as individuals and treats a set of reference interference patterns as individuals.

FIG. 10 shows an example of another specific option for carrying out comparison step 240. The example of FIG. 10, like that of FIG. 7, is based on a depth scan (FIG. 4) but applies to any of the foregoing or similar methods which involve sampling the tissue at multiple sample sites (e.g. the depth scan of FIG. 4, the area scan of FIG. 5 or the volumetric scan of FIG. 6). Block 206 shows the result of having recorded the sample interference patterns $P_{001}$ through $P_{00n}$ arising from an n-level depth scan. Once the depth scan is complete (block 210), the method proceeds to comparison block 240. The comparison step at block 240 treats the sample interference patterns individually and compares the individual sample interference patterns to individual members of the reference interference pattern array. The individualized nature of the comparison is indicated at block 240 by the use of borders that surround each interference pattern individually. The comparison step 240 carries out individual comparisons ($P_{001}$ to $C_{11}$, $P_{002}$ to $C_{12}$, ... $P_{00n}$ to $C_{1n}$) rather than the aggregate comparison of FIG. 7.

Figure 11:
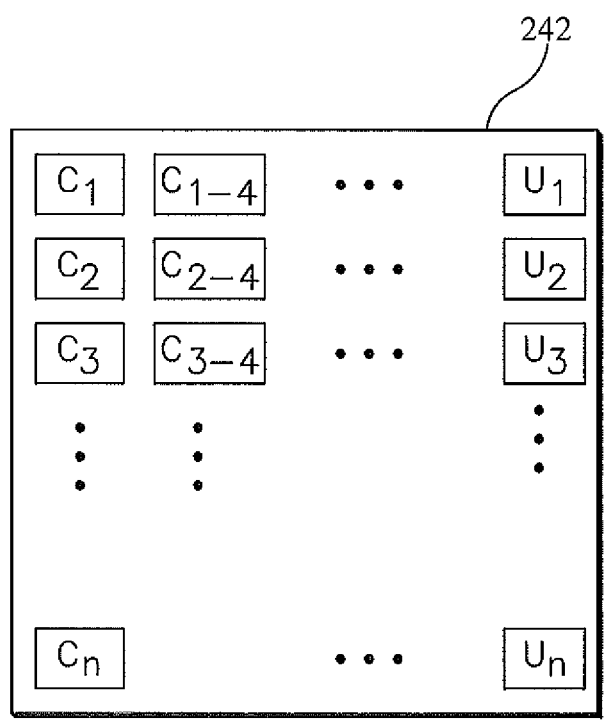
FIG. 11 is a block representing a library which may be employed by the methods described herein.

FIG. 11 elaborates on the library of interference patterns. Library entries $C_1, C_2, \ldots C_n$ correspond to the interference patterns of known tissue conditions where each subscript corresponds to a particular condition. As already noted a second subscript may be used to indicate depth d. The library also includes entries $C_{1-4}$, $C_{2-4}$ where the hyphenation indicates that the sample exhibits two conditions (e.g. condition number 1 and condition number 4). Once again each condition subscript can include a second digit to indicate depth. Library entries $U_1$ through $U_n$ indicate unknown conditions, i.e. the entry is based on a tissue sample which has been evaluated but does not appear to be either normal or representative of a known condition.

Figure 12:
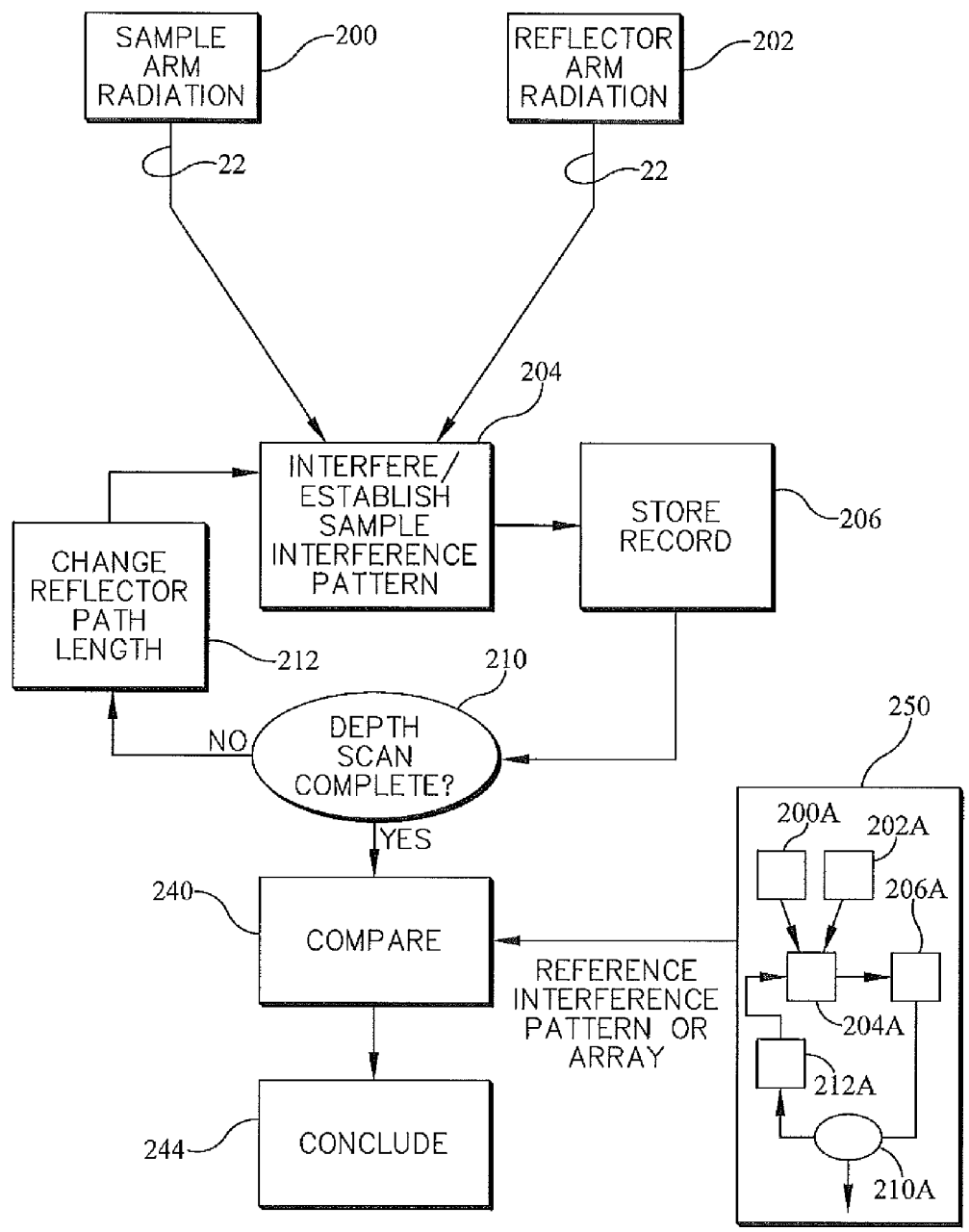
FIG. 12 is a block diagram similar to that of FIG. 4 showing a step of actively establishing the reference interference patterns in lieu of using a pre-existing library of reference interference patterns.
Figure 13:
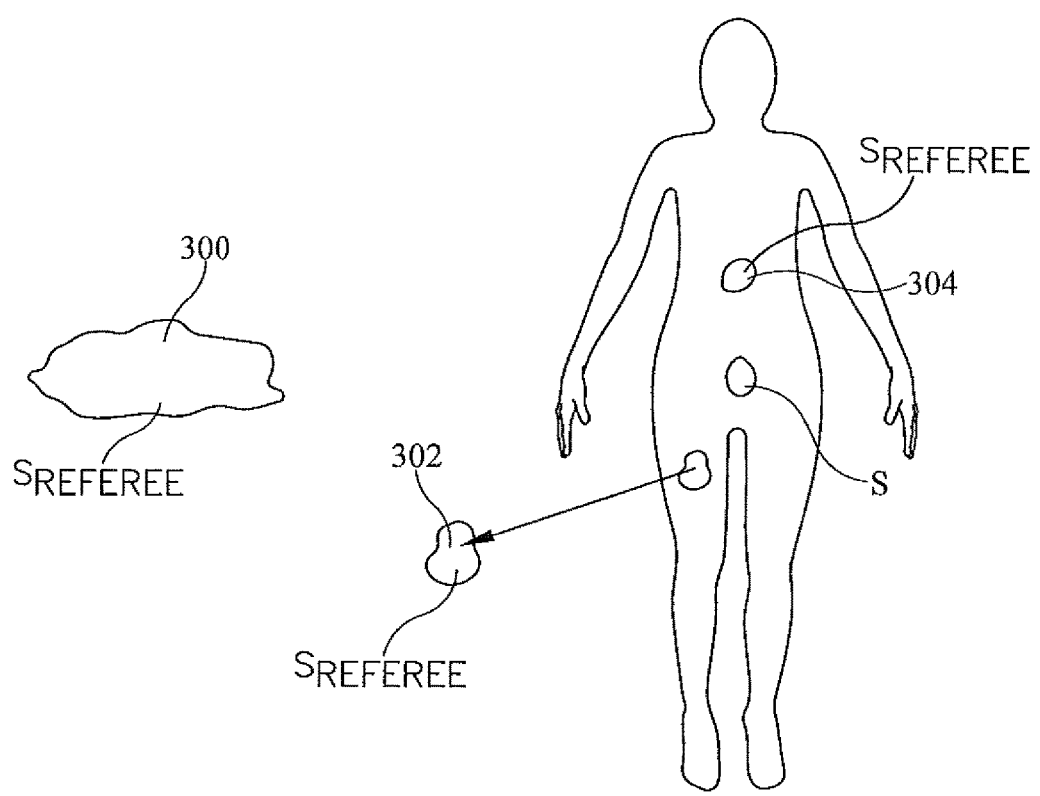
FIG. 13 is an illustration showing possible sources of a referee tissue sample for use in the method illustrated in FIG. 12.

FIGS. 12-13 show an option which may be used as an alternative to using an existing library 242 of reference interference patterns. The alternative method includes the step of actively establishing or generating the one or more reference interference patterns at block 250 rather than using a pre-existing library. Accordingly, this alternative will be referred to as the "active" method. As seen in FIG. 12 the step of establishing the reference interference pattern includes substeps 200A, 202A, 204A, 206A, 210A, 212A, analogous to the similarly numbered steps already described in connection with inspecting the tissue sample S of concern. However the substeps are applied to a referee sample $S_{REFEREE}$. The substeps establish the interference pattern of the referee sample. The interference pattern of the referee sample is then communicated to comparison block 240 where it is compared to the interference pattern of the tissue sample of interest.

The active method may be useful when there is reason to believe that a particular condition of interest or concern is present in the sample S. In one variant the established referee interference pattern corresponds to a tissue condition known or believed to be present in a referee tissue sample $S_{REFEREE}$. In that case a favorable comparison between the interference pattern of the sample S and the interference pattern of the referee sample at block 240 suggests that the known or believed condition is present in the sample S. An unfavorable comparison suggests that the known or believed condition is not present in the sample (although some other condition may be). In another variant the referee tissue sample may be one that is considered to be a healthy tissue sample, at least with respect to the condition of interest. In that case a favorable comparison at block 240 reveals that tissue sample S exhibits the same degree of health as the referee sample. An unfavorable comparison suggests some difference between the sample S and the healthy referee sample, but may be otherwise inconclusive.

Referring to FIG. 13, irrespective of whether the referee sample is believed to exhibit a condition of interest or is considered to be healthy, the referee sample may be a previously acquired specimen 300 from the person under evaluation or from another person. Alternatively the referee sample may be a real-time sample from the person whose tissue is under evaluation. The real-time referee sample may be excised from the person (referee sample 302) or it may be an in-situ sample (referee sample 304) from another site on the person's body which may be an anatomically comparable site. An anatomically comparable site is a site different from the site of sample S but which, when healthy, is believed to exhibit the same or similar light scattering properties as healthy tissue at the sample site. Additionally or alternatively the comparable site may be one which, when distressed by an unhealthy condition, is believed to exhibit the same or similar light scattering properties as tissue at the sample site distressed by the same unhealthy condition. The referee sample may also be a historical, in-situ sample. A historical in-situ referee sample is a region of tissue whose interference pattern M was established at an earlier time. When a historical sample is used the sample of interest S may be the same region of tissue as the historical sample. Alternatively the sample of interest S could be from another region of the person's body. In another alternative the referee sample is based on a different person and may be at an anatomical site corresponding to the anatomical site of interest on the patient, or may be at a comparable anatomical site.

When the tissue sample S whose condition is sought and the referee sample $S_{REFEREE}$ are from the same person, the site of sample S can be referred to as the target site and the site of the referee sample can be referred to as a sister site. A sister site is one whose tissue is believed to be a reasonably accurate surrogate for healthy tissue at the target site. Table 1 below shows one or more sister sites for a number of target sites.

TABLE 1

| Target Site | Sister Site |
| --- | --- |
| Left or right heel | Opposite (right or left) heel |
| Sacrum | Gluteus, offset laterally from sacrum, or Sternum |
| Any site where the tissue condition is a condition of interest | Same site at an earlier time. |

The above described active method has been presented as an alternative to using a library of interference patterns. However an interference pattern developed according to the active method may be used in cooperation with the interference patterns from the library. In one such mode of use the interference pattern developed under the active method is used to conduct a validation check of the method based on the library of interference patterns, or vice versa. In another mode of use the interference pattern developed under the active method is used as if it were just another member of the library.

Although this disclosure refers to specific embodiments, it will be understood by those skilled in the art that various changes in form and detail may be made without departing from the subject matter set forth in the accompanying claims.

We claim:

1. A method of assessing a tissue sample comprising: splitting source electromagnetic radiation into:
   a) sample arm radiation directed in a Z direction toward an in-situ tissue sample whose condition is sought thereby illuminating the sample at a first selected XY coordinate pair of the sample, and
   b) reflector arm radiation directed toward a reflector so that the reflector arm radiation travels a path length; interfering sample-scattered electromagnetic radiation with reflector-reflected electromagnetic radiation thereby establishing an interference pattern associated with the in-situ sample;
   generating a reference interference pattern or patterns, each generated interference pattern being associated with an in-situ referee tissue sample whose condition with respect to a condition of interest is known or believed; comparing the sample interference pattern to the generated reference interference pattern; and
   reaching a conclusion about the sample based on the comparison; wherein the tissue sample whose condition is sought is at a target site and the referee tissue sample is at one or more sister sites the target site being the sacrum and the sister site being the gluteus, offset laterally from the sacrum, or the sternum.

2. The method of claim 1 comprising two or more of the establishing steps, the establishing steps being carried out for different path lengths, and wherein the reference interference pattern is a pattern array, and wherein the comparing step comprises comparing sample interference patterns arising from the two or more establishing steps to members of the reference interference pattern array.

3. The method of claim 2 wherein the two or more establishing steps are carried out at one or more additional XY coordinate pairs different from the first XY coordinate pair.

4. The method of claim 2 wherein the comparing step treats the sample interference patterns as an aggregate and compares the aggregate to the reference interference pattern array as a whole.

5. The method of claim 2 wherein the comparing step treats the sample interference patterns individually and compares the individual patterns to members of the reference interference pattern array taken individually.

6. The method of claim 1 comprising two or more of the establishing steps, the establishing steps being carried out for substantially equal path lengths at one or more additional XY coordinate pairs different from the first XY coordinate pair, and wherein the reference interference pattern is a pattern array, and wherein the comparing step comprises comparing sample interference patterns arising from the two or more establishing steps to the reference interference pattern array.

7. The method of claim 6 wherein the two or more establishing steps are carried out for different path lengths.

8. The method of claim 6 wherein the comparing step treats the sample interference patterns as an aggregate and compares the aggregate to the reference interference pattern array as a whole.

9. The method of claim 6 wherein the comparing step treats the sample interference patterns individually and compares the individual patterns to members of the reference interference pattern array taken individually.

10. The method of claim 1 wherein the conclusion is whether or not a pressure ulcer or a condition consistent with an incipient pressure ulcer is present in the sample.

11. The method of claim 1 wherein the source electromagnetic radiation is selected from a portion of the electromagnetic spectrum which encompasses infrared, visible and ultraviolet wavelengths.

12. The method of claim 1 wherein the coherent electromagnetic radiation is low coherence electromagnetic radiation.

* * * * *